United States Patent [19]

Dwyer et al.

[11] 4,361,503

[45] Nov. 30, 1982

[54] CATALYST FOR CONVERTING SYNTHESIS GAS TO HIGH OCTANE PREDOMINANTLY OLEFINIC NAPHTHA

[75] Inventors: Francis G. Dwyer, West Chester, Pa.; William E. Garwood, Haddonfield, N.J.

[73] Assignee: Mobil Oil Corporation, New York, N.Y.

[21] Appl. No.: 220,923

[22] Filed: Dec. 29, 1980

Related U.S. Application Data

[63] Continuation-in-part of Ser. No. 76,027, Sep. 17, 1979, abandoned, which is a continuation of Ser. No. 926,987, Jul. 21, 1979, Pat. No. 4,172,843.

[51] Int. Cl.$^3$ .......................... B01J 29/28; B01J 29/30
[52] U.S. Cl. ................................................. 252/455 Z
[58] Field of Search ..................... 252/455 Z; 518/717

[56] References Cited

U.S. PATENT DOCUMENTS

| | | | |
|---|---|---|---|
| 3,254,023 | 5/1966 | Miale et al. | 518/717 X |
| 4,138,442 | 2/1979 | Chang et al. | 518/717 X |
| 4,159,995 | 7/1979 | Haag et al. | 518/717 |

*Primary Examiner*—Carl F. Dees
*Attorney, Agent, or Firm*—Charles A. Huggett; Michael G. Gilman; Van D. Harrison, Jr.

[57] ABSTRACT

An improved catalyst composition is disclosed for converting synthesis gas to hydrocarbon mixtures. The catalyst comprises an iron-containing, Fischer-Tropsch catalyst and a crystalline zeolite having a silica-to-alumina ratio of greater than 200 (including zeolites containing essentially no alumina) and an $(R_2O+M_{2/n}O):SiO_2$ rate of less than 1.1:1 where M is a metal other than a metal of Group IIIA, n is the valence of said metal, and R is an alkyl ammonium radical, said organosilicate being characterized by a specified x-ray diffraction pattern.

8 Claims, No Drawings

CATALYST FOR CONVERTING SYNTHESIS GAS TO HIGH OCTANE PREDOMINANTLY OLEFINIC NAPHTHA

This application is a continuation-in-part of our copending application Ser. No. 076,027, filed Sept. 17, 1979, now abandoned which is a continuation of application Ser. No. 926,987, filed July 21, 1979, now U.S. Pat. No. 4,172,843.

BACKGROUND OF THE INVENTION

1. Field of the Invention

This invention is concerned with an improved process for converting synthesis gas, i.e., mixtures of gaseous carbon oxides with hydrogen or hydrogen donors, to hydrocarbon mixtures. This invention is further concerned with the catalyst composition which can be utilized in effecting this conversion.

2. Description of the Prior Art

Processes for the conversion of coal and other hydrocarbons such as natural gas to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353-433 (1966), Interscience Publishers, New York, New York.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

The conversion of synthesis gas into valuable products can be greatly enhanced by employing a special type of crystalline aluminosilicate zeolite exemplified by ZSM-5 or ZSM-11 in admixture with a conventional Fischer-Tropsch catalyst. Thus, for example, in copending application Ser. No. 463,711, filed Apr. 24, 1974, abandoned, but parent to U.S. Pat. No. 4,086,262, issued Apr. 25, 1978, and a parent to U.S. Pat. No. 4,096,163, issued June 20, 1978 there is disclosed a process for the conversion of syngas by passing the same at elevated temperature over a catalyst which comprises an intimate mixture of a Fischer-Tropsch component and a special type of zeolite such as ZSM-5. Said copending application points out that the products produced are hydrocarbon mixtures which are useful in the manufacture of heating oil, high octane gasoline, aromatic compounds and chemical intermediates.

As can well be appreciated, the patent and technical literature relating to the Fischer-Tropsch process, is, indeed, extensive and the various catalysts reported in the prior art have been used by themselves as well as in admixture with catalytically inactive supports such as kieselguhr. Although the reasons for using catalytically inactive supports have varied, nevertheless, it would appear that one reason for using the same was that it resulted in increased surface area of the Fischer-Tropsch component upon which it was deposited or admixed and that it also aided in controlling the heat requirements of the overall exothermic reactions.

It is also known in the art to admix a Fischer-Tropsch component with a material, such as silica alumina which is known to be catalytically active for the conversion of hydrocarbons.

U.S. Pat. No. 2,637,739 discloses a Fischer-Tropsch process involving the conversion of syngas by passing the same over a Fischer-Tropsch catalyst in admixture with silica alumina.

U.S. Pat. No. 3,894,102 is directed towards a two-stage process for the conversion of syngas wherein the first stage a methanol synthesis catalyst is admixed with an acidic dehydrogenation catalyst and the product thereof contacted with an HZSM-5 type aluminosilicate zeolite.

In copending application Ser. No. 793,015, filed May 2, 1977 now abandoned, there is disclosed a method for producing an olefinic gasoline by contacting a syngas with a catalyst mixture comprising two components, one being a cobalt containing Fischer-Tropsch component and the other being a ZSM-5 type aluminosilicate zeolite wherein the activity of the ZSM-5 type aluminosilicate zeolite is balanced with the activity of the cobalt containing Fischer-Tropsch component. The product resulting from this type of conversion is an olefinic gasoline wherein the olefins are predominantly branched (>50 percent) and internal due to the action of the ZSM-5 type component.

In copending application Ser. No. 793,016, filed May 2, 1977 now abandoned, but parent to U.S. Pat. No. 4,304,871 issued Dec. 8, 1981, there is disclosed a method for producing an olefinic gasoline by contacting a syngas with a catalyst mixture comprising two components, one being an iron-containing Fischer-Tropsch component and the other being a ZSM-5 type aluminosilicate zeolite wherein the activity of the ZSM-5 type aluminosilicate zeolite is balanced with the iron-containing Fischer-Tropsch component. The product resulting from this type of conversion is an olefinic gasoline having a clear research octane number greater than 85 wherein the olefins are predominantly branched (>50 percent) and internal due to the action of the ZSM-5 type of component.

Also copending is application Ser. No. 775,129, filed Mar. 7, 1977 now U.S. Pat. No. 4,269,783 issued Mar. 7, 1977 which is concerned with the conversion of syngas over a catalyst comprising a Fischer-Tropsch component and an acidic cracking catalyst and is also directed towards balancing the activity of the acidic component with the Fischer-Tropsch catalyst. However, the product obtained from the process of said copending application is an olefinic product wherein the olefins have predominantly internal (>50 percent) double bonds and the gasoline has a clear research octane number greater than 75. The solid acidic component utilized in the process of this copending application is not a ZSM-5 type zeolite, but rather it includes the use of an amorphous material, such as silica alumina, as well as the more conventional type crystalline aluminosilicates, such as faujasite, erionite, mordenite, etc., that are capable of sorbing n-hexane.

U.S. Pat. No. 3,013,990 suggests a catalyst composition useful in processes including Fischer-Tropsch synthesis (see Column 10, lines 71-74) which composition comprises a zeolite molecular sieve containing a substantial quantity of at least one material selected from the group consisting of Fe, Co, Ni, and oxides thereof in the internal adsorption area of the zeolite molecular sieve. At Column 1, lines 38-39, "zeolitic molecular sieves" are defined as "metal aluminosilicates", and all the zeolites disclosed have a relatively high ratio of alumina:silica. None of the zeolites have the composition or characteristic x-ray powder diffraction pattern of the silica zeolite component recited in the present claims. Moreover, the patent does not discuss the preparation of gasoline-boiling-range hydrocarbons.

The ZSM-5 type crystalline zeolite component of the intimate catalyst mixture recited in the present claims is disclosed in U.S. Pat. No. 3,941,871. The uses suggested therein for the crystalline zeolite catalyst are hydrocracking, catalytic cracking, reforming, hydroisomerization of normal paraffins, and olefin isomerization (Column 5, line 54 to Column 6, line 22). No process is discussed for the direct conversion of synthesis gas to gasoline-boiling-range products.

SUMMARY OF THE INVENTION

The novel process of this invention is an improved process for converting syngas to more valuable hydrocarbons in that it employs a special catalyst comprising a crystalline zeolite having a silica-to-alumina ratio of greater than 200 and an $(R_2O+M_{2/n}O):SiO_2$ ratio of less than 1.1:1 where M is a metal other than a metal of Group IIIA, n is the valence of said metal, and R is an alkyl ammonium radical, said zeolite being characterized by a special x-ray diffraction pattern. Although the crystalline zeolite has been described as having a silica-to-alumina ratio of greater than 200:1, it will be understood that the zeolite may contain no alumina. A specific embodiment of this invention is directed towards the formation of a very specific product. The liquid product of this embodiment, like that of copending patent application Ser. Nos. 793,015 and 793,016, is a high-octane, predominantly-olefinic naphtha having a boiling range of less than 400° F. at a 90 percent overhead which is defined as a $C_5+$ naphtha with an aromatic content of less than 15-20 weight percent, an olefin-plus-aromatics content exceeding 50 weight percent wherein >50 percent of the olefins (based on total pentenes) have a branched chain structure and an internally-positioned double bond, and the gasoline has a clear research octane number greater than 85.

The present invention is further concerned with obtaining the above-defined product in good yields and good selectivities from the starting syngas material.

The present invention is still further concerned with a catalyst composition comprising potassium-promoted iron intimately admixed with a crystalline zeolite which catalyst composition is useful for converting synthesis gas to olefinic gasoline.

Prior teachings regarding the conversion of synthesis gas to olefinic gasoline have been based on the use of potassium-deactivated ZSM-5 catalysts as exemplified by copending application Ser. No. 793,015 and Ser. No. 793,016 described supra. The discovery of the present invention is that a desirable alternative to such processes is to employ a crystalline silicate as the zeolite component of a zeolite/Fischer-Tropsch component catalyst composition for syngas conversion.

DETAILED DESCRIPTION OF THE INVENTION

The materials known to reduce carbon monoxide to oxygenated or olefinic hydrocarbon products that have at least one carbon-to-carbon bond in their structure include zinc, iron, cobalt, ruthenium, thorium, rhodium, and osmium. With the exception of ruthenium, all practical art-recognized synthesis catalysts contain chemical and structural promoters. These promoters include copper, manganese, chromia, alumina, the alkaline earths, the rare earths, and alkali. Alkali, e.g., the carbonates of Group IA of the Periodic Table, and especially potassium, is of particular importance for use as promoters with iron catalysts. Potassium-modified iron Fischer-Tropsch catalyst greatly reduces the conversion to methane. Supports such as kieselguhr sometimes act beneficially.

The crystalline zeolite component of the catalyst arrangement is substantially free of alumina, but may contain very minor amounts of such oxide attributable primarily to the presence of aluminum impurities in the reactants and/or equipment employed. Thus, the molar ratio of alumina to silica will be in the range of 0 to less than 0.005 mole of $Al_2O_3$ to more than 1 mole of $SiO_2$. Generally the latter may range from $>1$ $SiO_2$ up to 500 or more. Broadly, the $SiO_2/Al_2O_3$ ratio is greater than about 200/1. Preferably, the ratio is greater than about 500/1 and, more preferably is about 1300/1 or more. Preparation of the crystalline zeolite component is described in U.S. Pat. No. 3,941,871, the entire content of which is incorporated herein by reference.

That patent provides a family of crystalline zeolites which are essentially free of Group IIIA metals, i.e., aluminum and/or gallium. These zeolites have surprisingly been found to be characterized by an x-ray diffraction pattern characteristic of the ZSM-5 type crystalline aluminosilicates. The method described in U.S. Pat. No. 3,941,871 may also be used to prepare crystalline zeolites of the ZSM-11 type which are essentially free of Group IIIA metals. Similar to the crystalline zeolites described in the '871 patent, these zeolites are characterized by an x-ray diffraction pattern characteristic of the ZSM-11 type crystalline aluminosilicates, which are described in U.S. Pat. No. 3,709,979, the entire content of which is incorporated herein by reference. In addition to having these characteristic x-ray diffraction patterns, the crystalline zeolites of the present invention can be identified in their anhydrous state in terms of mole ratios of oxides as follows:

(1) A $SiO_2:Al_2O_3$ ratio of greater than 200:1 and
(2) an $(xR_2O+(1-x)M_{2/n}O):SiO_2$ ratio of less than 1.1:1 where M is a metal other than a metal of Group IIIA, n is the valence of said metal, and R is an alkyl ammonium radical and x is greater than 0 but not exceeding 1. Preferably R is a tetraalkyl ammonium radical, the alkyl groups of which contain 2-5 carbon atoms.

In the above composition, $R_2O$ and $M_{2/n}O$ may be removed by replacement with or conversion to other desired components which serve to enhance catalytic activity, stability and/or sorption or absorption characteristics. It is particularly contemplated that R and/or M may be at least partially in the ammonium form as a result of ion exchange.

As above noted, the families of crystalline zeolites disclosed and claimed herein have definite x-ray diffraction patterns. Such x-ray diffraction patterns, similar to those for the ZSM-5 and ZSM-11 zeolites, show the following significant lines:

TABLE 1

ZSM-5 TYPE CRYSTALLINE ZEOLITE

| Interplanar Spacing d(A): | | Relative Intensity |
|---|---|---|
| 11.1 | ±0.2 | s |
| 10.0 | ±0.2 | s |
| 7.4 | ±0.15 | w |
| 7.1 | ±0.15 | w |
| 6.3 | ±0.1 | w |
| 6.04 | | |
| 5.97 | ±0.1 | w |
| 5.56 | ±0.1 | w |
| 5.01 | ±0.1 | w |
| 4.60 | ±0.08 | w |
| 4.25 | ±0.08 | w |
| 3.85 | ±0.07 | vs |
| 3.71 | ±0.05 | s |
| 3.04 | ±0.03 | w |
| 2.99 | ±0.02 | w |
| 2.94 | ±0.02 | w |

TABLE 2

ZSM-11 TYPE CRYSTALLINE ZEOLITE

| Interplanar Spacing d(A): | | Relative Intensity |
|---|---|---|
| 11.2 | ±0.2 | m |
| 10.1 | ±0.2 | m |
| 6.73 | ±0.2 | w |
| 5.75 | ±0.1 | w |
| 5.61 | ±0.1 | w |
| 5.03 | ±0.1 | w |
| 4.62 | ±0.1 | w |
| 4.39 | ±0.08 | w |
| 3.86 | ±0.07 | vs |
| 3.73 | ±0.07 | m |
| 3.49 | ±0.07 | w |
| (3.07,3.00) | ±0.05 | w |
| 2.01 | ±0.02 | w |

The parentheses around lines 3.07 and 3.00 in Table 2 indicate that they are separate and distinct lines, but are often superimposed. The values were determined by standard techniques. The radiation was the K-alpha doublet of copper and a Geiger Counter Spectrometer with a strip chart pen recorder was used. The peak heights, I, and the positions as a function of two times theta, where theta is the Bragg angle, were read from the spectrometer chart. From these, the relative intensities, 100 $I/I_0$, where $I_0$ is the intensity of the strongest line or peak and d(obs.), the interplanar spacing in A, corresponding to the recorded lines were calculated. In Table I the relative intensities are given in terms of the symbols s=strong, w=weak and vs=very strong.

The crystalline zeolites can be used either in the alkali metal form, e.g., the sodium form or other desired metal form, the ammonium form or the hydrogen form. Preferably, one of the last two forms is employed. The cation content should in no case be so large as to substantially eliminate the activity of the zeolite for the catalysis being employed in the instant invention. For example, a completely sodium exchanged ZSM-5 or ZSM-11 appears to be largely inactive for shape selective conversions required in the present invention.

The specific zeolites described, when prepared in the presence of organic cations, are substantially inactive, possibly because the crystalline free space is occupied by organic cations from the forming solution. The zeolites as synthesized or after impregnation can be beneficially converted to another form by thermal treatment. This can be done by heating to a temperature in the range of 200° to 600° C. in an atmosphere such as air, nitrogen, etc. and at pressures ranging from subatmospheric to above-atmospheric for between 1 and 48 hours. Dehydration may also be performed at lower temperatures merely by placing the zeolite in a vacuum, but a longer time is required to obtain a sufficient amount of dehydration.

The crystalline zeolites as synthesized can have the original components thereof replaced by a wide variety of others according to techniques well known in the art. Typical replacing components would include hydrogen, ammonium, alkyl ammonium and aryl ammonium and metals, other than metals of Group IIIA, including mixtures of the same. The hydrogen form may be prepared, for example, by substitution of original sodium with ammonium. The composition is then calcined at a temperature of, say, 1000° F., causing evolution of ammonia and retention of hydrogen in the composition. Of the replacing ions, preference is accorded to metals of Groups II, IV and VIII of the Periodic Table with the caveat that trivalent and tetravalent forms of Group IV and VIII metals may not be suitable "replacing components."

The crystalline zeolites are then preferably washed with water and dried at a temperature ranging from 150° F. to about 600° F. and thereafter calcined in air or other inert gas at temperatures ranging from 500° F. to 1500° F. for periods of time ranging from 1 to 48 hours or more.

Regardless of the synthesized form of the zeolite, the spatial arrangement of atoms which form the basic crystal lattices remain essentially unchanged by the described replacement of sodium or other alkali metal or by the presence in the initial reaction mixture of metals in addition to sodium, as determined by an x-ray powder diffraction pattern of the resulting zeolite. The x-ray diffraction patterns of such products are essentially the same as those set forth in Table 1 or Table 2 above.

The crystalline zeolites prepared in accordance with the instant invention are formed in a wide variety of particular sizes. Generally, the particles can be in the form of powder, a granule, or a molded product such as an extrudate having a particle size sufficient to pass through a 2 mesh (Tyler) screen and be maintained on a 400 mesh (Tyler) screen in cases where the catalyst is molded such as by extrusion. The zeolite can be extruded before drying or dried or partially dried and then extruded.

As has been previously set forth, a particular aspect of this invention resides in the production of a particular product utilizing a catalyst mixture comprised of an iron Fischer-Tropsch component and a crystalline zeolite component. The catalyst mixtures contemplated may be prepared in various ways. The two components may be separately prepared in the form of catalyst particles such as pellets or extrudates, for example, and then mixed in the required proportions. The particle size of the individual component particles may be quite small, for example, from about 0.01 to about 300 microns, when intended for use in fluid bed operation; or they may be as large as up to about ½ inch for fixed bed operation. The two components may also be mixed as powders in desired proportions and formed into pellets or extrudate, each pellet containing both components in substantially the required proportions. Binders such as clays may be added to the mixture. Alternatively, the component that has catalytic activity for the reduction of carbon monoxide may be formed on the acidic crystalline zeolite component by conventional means such as impregnation of that solid with salt solutions of the desired metals, followed by drying and calcination. Base exchange of the acidic crystalline zeolite component also may be used in some selected cases to effect the introduction of part or all of the carbon monoxide reduction component. Other means for forming the intimate mixture may be used, such as: precipitation of the carbon monoxide reduction component in the presence of the acidic crystalline zeolite, electrolytic deposition of metal on the zeolite, or deposition of metal from the vapor phase. Various combinations of the above preparative methods will be obvious to those skilled in the art of catalyst preparation.

In copending application Ser. No. 729,938, filed Oct. 6, 1976 now abandoned, but parent to U.S. Pat. No. 4,304,871 issued Dec. 8, 1981, it is demonstrated that for the production of aromatic gasoline from synthesis gas the iron catalyst component is preferaby retained in an arrangement wherein it is surrounded by a relatively large proportion of crystalline zeolite component. The same type of configuration is preferred in this invention, particularly under fixed bed operating conditions. The crystaline zeolite-containing component is so arranged to statistically promote the sequential reaction mechanism of synthesis gas conversion to primarily olefin intermediates by the iron catalyst followed by chain growth of the olefin intermediate with the modified zeolite catalyst component to form branched chain and internal olefins in preference to aromatics and before the olefin intermediate has a chance to contact additional particles of iron catalyst. Thus, the abundance of zeolite particles about the iron particle intercepts the olefin intermediate of iron catalyst conversion before the olefin intermediate can build up into long-chain linear wax molecules. Supporting evidence for the above-identified reaction sequence and catalyst component arrangement promoting the scavenging function by the zeolite catalyst component is provided by related studies on propylene or methanol conversion to form aromatics with a ZSM-5 crystalline aluminosilicate zeolite. The fact that the zeolite component provides a scavenging function when properly proportioned with respect to the carbon monoxide reducing component is further supported by data obtained with the heterogeneous catalyst mixture after treatment of particularly the zeolite component to substantially eliminate the aromatizing function.

The novel process of this invention is carried out at temperatures ranging from about 450° F. and more preferably at least 550° F. to about 750° F. such that no more than about 30 weight percent of methane plus ethane is formed. Gas hourly space velocities (GHSV) range from 500 to 20,000 and more desirably from 1000 to 6000 based on fresh feed and total catalyst volume. Hydrogen to carbon oxides ratios can vary from 0.5 to 6.0 and more preferably from 1.0 to 2.0. Pressures range from 50 to 1000 psig and more preferably from 150 to 400 psig. The ratio of the Fischer-Tropsch component to the acidic solid (zeolite plus binder) is not narrowly critical and can range from 1.0 to a practical maximum of 20 volumes of the acidic solid per volume of the Fischer-Tropsch component. A particularly desirable range is from 2 to 10 volumes of acidic solid per volume of Fischer-Tropsch component.

Operating within the above referred-to parameters will result in a process wherein at least 50 percent of the carbon monoxide in the fresh feed is actually converted. Since theoretical conversions vary with syngas composition, a preferred conversion range on the fresh feed is at least 50 percent of the carbon monoxide and of the hydrogen based on theoretical.

The following Examples 1-5 are limited primarily to one representative pressure, 200 psig; and a GHSV range of 1500 to 3400 based on active reagents, which is considerably higher than normally used for commercial fixed bed operation. These conditions are not, of course, optimum for demonstrating temperature limits of process operability. Fresh feed GHSV of 500 and even less are recorded in Fischer-Tropsch process literature. Obviously, if the GHSV were reduced from 3500 to 500, the operating temperature could be reduced substantially below 500° F. before losing FeK and/or zeolite activity.

EXAMPLES 1-5

Syngas with a hydrogen to carbon monoxide ratio of 2 was contacted at a 600° F. catalyst bed setting, a pressure of 200 psig and a gas hour space velocity (GHSV) of 3200-3600 with various aluminosilicate and silicate ZSM-5-type catalysts intimately mixed with Fe(K). In all Examples, the ZSM-5-type component was sized to 12-25 mesh and 1.6 cc of the sized ZSM-5-type component was mixed with 0.4 cc of 12-25 mesh Girdler G-82 Fe(K). The runs were monitored and the products measured and analyzed. Results are shown in Table 3 below. The ZSM-5-type component of Examples 1, 2, 3, and 4 were bound with 35 weight percent Catapal alumina and extruded as 1/16" extrudates. The ZSM-5-type component of Example 5 is the pure acid form of the silicate ZSM-5-type component. Examples 1 and 2 are comparative examples showing syngas conversion over an Fe(K)/aluminosilicate ZSM-5-type component. Examples 3-5 show syngas conversion according to the process of the present invention over an Fe(K)/silicate ZSM-5-type component.

Comparing Examples 1, 3, and 4, it may be seen that the main effect of increasing $SiO_2/Al_2O_3$ ratio is to decrease aromatic make. Aromatization is related to site density. Site strength appears to vary exponentially with $SiO_2/Al_2O_3$ ratio since a semilog plot of $C_{6}+$ aromatics produced in Examples 1, 3 and 4 as a function of $SiO_2/Al_2O_3$ ratio is nearly a straight line.

The catalyst of Example 2 (70/1 $SiO_2/Al_2O_3$ ZSM-5 extrudate (35 percent binder) poisoned with potassium) has performed well in separate particle, fixed bed operation. However, attempts to put the K-deactivated 70/1 $SiO_2/Al_2O_3$ ZSM-5 into the same particle with <250 $\mu$Fe(K) have failed because of excessive methane formation. Comparing Examples 2 and 5, it will be noted that the 1600/1 pure $SiO_2$ crystalline zeolite differs only slightly from the K-deactivated, 70/1 $SiO_2/Al_2O_3$ ZSM-5 and is a desirable alternative to the latter catalyst for syngas conversion.

TABLE 3

| ZSM-5-type Catalyst Component Description | Example | | | | |
|---|---|---|---|---|---|
| | 1<br>65% SiO$_2$—<br>Al$_2$O$_3$ ext. | 2<br>K(0.95%)—<br>SiO$_2$—Al$_2$O$_3$<br>ext. | 3<br>65% SiO$_2$<br>ext. | 4<br>65% SiO$_2$<br>ext. | 5<br>Pure SiO$_2$<br>crystalline<br>zeolite |
| SiO$_2$/Al$_2$O$_3$ ratio in ZSM-5-type component | 70 | 70 | 500 | 1600 | 1600 |
| Run Time (Hrs.) | 24 | 23 | 24 | 23.5 | 22¾ |
| Accum. Time (Days) | 2.0 | 1.8 | 1.8 | 1.8 | 1.7 |
| GHSV | 3420 | 3215 | 3280 | 3375 | 3580 |
| WHSV | 1.62 | 1.54 | 1.50 | 1.53 | 1.89 |
| Temp. (°F.), Ave. | 618 | 620 | 619 | 621 | 626 |
| Hot Spot | 628 | 628 | 624 | 629 | 636 |
| CO Conv. (wt. %) | 95 | 97 | 96 | 97 | 94 |
| H$_2$ Conv. (wt. %) | 54 | 59 | 53 | 54 | 45 |
| Hydrocarbon Composition (wt. %) | | | | | |
| C$_1$ | 17 | 17 | 20 | 17 | 18 |
| C$_2$ | 4 | 6 | 7 | 6 | 8 |
| C$_3$ | 8 | 4 | 5 | 4 | 6 |
| C$_4$ | 18 | 11 | 12 | 12 | 14 |
| C$_5$ | 11 | 10 | 12 | 12 | 13 |
| C$_6$+ | 42 | 52 | 44 | 49 | 41 |
| Olefins (wt. % by C no.) | | | | | |
| C$_2$ | 6 | 26 | 33 | 32 | 40 |
| C$_3$ | 7 | 45 | 28 | 46 | 53 |
| C$_4$ | 4 | 53 | 54 | 56 | 68 |
| C$_5$ | 3 | 57 | 57 | 63 | 74 |
| C$_5$ Olefin Dist. (wt. %) | | | | | |
| 1-C$_5$= | — | 3 | 3 | 2 | 3 |
| T + C$_2$C$_5$= | 6 | 18 | 20 | 18 | 19 |
| MC$_4$= | 94 | 79 | 77 | 78 | 78 |
| C$_6$ + Aromatics (wt. %) | 50 | 13 | 21 | 14 | 13 |
| Liq. Prod. 90% B.P. (°F.) | 402 | 350 | 358 | 360 | 356 |
| C$_5$ + O.N. (R + O) | 92.1 | 92.0 | 92.1 | 91.7 | 92.6 |

We claim:

1. A catalyst composition comprising an iron-containing Fischer-Tropsch component and a volume excess of a solid containing a crystalline zeolite, wherein the crystalline zeolite comprises a zeolite having a composition in its anhydrous state in terms of mole ratios of oxides as follows:
   (a) an Al$_2$O$_3$:SiO$_2$ ratio within the range of from 0 to less than 0.005 Al$_2$O$_3$ to more than 1 SiO$_2$ and
   (b) an $(xR_2O+(1-x) M_{2/n}O)$:SiO$_2$ ratio of less than 1.1:1 where M is a metal other than a metal of Group IIIA, n is the valence of said metal, R is tetraalkylammonium and x is a number greater than 0 but not exceeding 1, said zeolite having the x-ray diffraction lines set forth in Table 1 or Table 2 of the specification.

2. The catalyst of claim 1 wherein M is sodium or sodium in combination with tin, calcium, nickel or zinc.

3. The catalyst of claim 1 wherein the volume ratio of said solid to said Fischer-Tropsch component is between 1 and 20.

4. The catalyst of claim 3 wherein said volume ratio is between 2 and 10.

5. The catalyst of claim 1 wherein the SiO$_2$:Al$_2$O$_3$ ratio of the crystalline zeolite is greater than about 200:1.

6. The catalyst of claim 1 wherein the SiO$_2$:Al$_2$O$_3$ ratio of the crystalline zeolite is greater than 500:1.

7. The catalyst of claim 1 wherein the SiO$_2$:Al$_2$O$_3$ ratio of the crystalline zeolite is greater than 1300:1.

8. The catalyst of claim 1 wherein the crystalline zeolite has been exchanged with ammonium ions.

* * * * *